United States Patent
Allen et al.

(10) Patent No.: US 11,363,004 B2
(45) Date of Patent: Jun. 14, 2022

(54) SECURE DEVICE RELAY

(71) Applicant: INTERNATIONAL BUSINESS MACHINES CORPORATION, Armonk, NY (US)

(72) Inventors: Corville O. Allen, Morrisville, NC (US); Kim Eric Wegner, Rochester, MN (US); Michele Chilanti, Rochester, MN (US)

(73) Assignee: International Business Machines Corporation, Armonk, NY (US)

(*) Notice: Subject to any disclaimer, the term of this patent is extended or adjusted under 35 U.S.C. 154(b) by 402 days.

(21) Appl. No.: 16/296,805

(22) Filed: Mar. 8, 2019

(65) Prior Publication Data
US 2020/0287878 A1   Sep. 10, 2020

(51) Int. Cl.
*H04L 29/06* (2006.01)
*H04L 9/40* (2022.01)
*H04L 9/32* (2006.01)
*H04L 9/08* (2006.01)
*G16H 80/00* (2018.01)

(52) U.S. Cl.
CPC ......... *H04L 63/0442* (2013.01); *G16H 80/00* (2018.01); *H04L 9/0825* (2013.01); *H04L 9/0827* (2013.01); *H04L 9/3247* (2013.01); *H04L 63/10* (2013.01); *H04L 63/18* (2013.01)

(58) Field of Classification Search
None
See application file for complete search history.

(56) References Cited

U.S. PATENT DOCUMENTS

| | | | |
|---|---|---|---|
| 7,039,810 B1 | 5/2006 | Nichols | |
| 7,181,017 B1 | 2/2007 | Nagel et al. | |
| 8,171,094 B2 | 5/2012 | Chan et al. | |
| 8,229,813 B2 | 7/2012 | Olin et al. | |
| 9,215,075 B1* | 12/2015 | Poltorak | H04L 63/04 |

(Continued)

FOREIGN PATENT DOCUMENTS

WO    2010132617 A3    11/2010

OTHER PUBLICATIONS

Alhayajneh et al., "Biometric Authentication and Verification for Medical Cyber Physical Systems", www.mdpi.com/journal/electronics, Electronics 2018, 7, 436; doi:10.3390/electronics7120436, pp. 1-17.

(Continued)

*Primary Examiner* — Andrew J Steinle
(74) *Attorney, Agent, or Firm* — Kristofer L. Haggerty

(57) ABSTRACT

Embodiments of the present invention disclose a method, a computer program product, and a computer system for providing a secure device relay between a data collection device and a server using a smart device. The present invention comprises transmitting to a server a unique identifier corresponding to a data collection device and a digital signature corresponding to a smart device. In addition, the present invention provides for receiving from the server a key pair and an exchange configuration defining access control to data stored on the data collection device. Moreover, the present invention includes transmitting to the data collection device a public key of the received key pair and the exchange configuration.

17 Claims, 6 Drawing Sheets

(56) References Cited

U.S. PATENT DOCUMENTS

| | | | |
|---|---|---|---|
| 2008/0224852 A1* | 9/2008 | Dicks | G16H 15/00 |
| | | | 340/539.12 |
| 2008/0235511 A1* | 9/2008 | O'Brien | H04L 9/0844 |
| | | | 713/171 |
| 2009/0063187 A1* | 3/2009 | Johnson | G16H 40/20 |
| | | | 705/2 |
| 2010/0235518 A1 | 9/2010 | Holden et al. | |

OTHER PUBLICATIONS

Mell et al., "The NIST Definition of Cloud Computing", National Institute of Standards and Technology, Special Publication 800-145, Sep. 2011, pp. 1-7.

Hanselman, "Diabetes Technology: Dexcom G5 CGM Review—So much wasted potential", https://www.hanselman.com/blog/DiabetesTechnologyDexcomG5CGM. . . , Oct. 13, 2015, pp. 1-7.

Entune Audio, "Phone Pairing, Compatibility and Use", https://www.toyota.com/entune/support/ea/phone-pairing/, printed Mar. 8, 2019, pp. 1-7.

Padgette et al., "Guide to Bluetooth Security", NIST Special Publication 800-121, Revision 2, https://doi.org/10.6028/NIST.SP.800-121r2, May 2017, pp. 1-67.

https://www.design-reuse.com/articles/39779/security-considerations-for . . . , "Security Considerations for Bluetooth Smart Devices", Ravikiran HV, PathPartner Technology Pvt.Ltd., printed Mar. 8, 2019, pp. 1-52.

https://www.b3cnewswire.com/201608041435/the-worlds-first-smart-ins . . . , The World's First Smart Insulin Pens with Automatic Wireless Data Transfer (868 MHz or Bluetooth), Aug. 4, 2016, pp. 1-3.

\* cited by examiner

SECURE DEVICE RELAY

BACKGROUND

The present invention relates generally to secure data exchange, and more particularly to securely exchanging data between a data collection device and a server using a smart device.

With the massive increase in electronic data storage of the last few decades, data has become a valuable commodity and data privacy has similarly become a large concern. Now, more than ever, greatest care is required when handling user data and, in particular, sensitive data such as personal healthcare data. As such, it is important that applications designed to exchange such data only have access to specific device data under specific conditions.

SUMMARY

Embodiments of the present invention disclose a method, a computer program product, and a computer system for providing a secure device relay between a data collection device and a server using a smart device. In particular, the present invention comprises transmitting to a server a unique identifier corresponding to a data collection device and a digital signature corresponding to a smart device. In addition, the present invention provides for receiving from the server a key pair and an exchange configuration defining access control to data stored on the data collection device. Moreover, the present invention includes transmitting to the data collection device a public key of the received key pair and the exchange configuration.

Embodiments of the present invention further comprise detecting an exchange request to exchange the data between the server and the data collection device, determining whether the exchange request is permitted based on the exchange configuration, and, based on determining that the exchange request is permitted by the exchange configuration, processing the request.

Further embodiments of the present invention further comprise, based on determining that the exchange request is not permitted by the exchange configuration, denying the exchange request and performing an action selected from a group comprising: notifying a user of the data collection device, notifying a physician of the user, and requesting consent to process the exchange from the user.

Aspects of the present invention further provide for receiving a request to modify access controls defined by the exchange configuration, obtaining consent to the requested modification from a user of the data collection device, and modifying the exchange configuration.

In embodiments, the exchange configuration defines access control with respect to a type of the data, an amount of the data, and a frequency at which the data is exchanged between the server and the data collection device.

In further embodiments, the exchange configuration further defines access control with respect to conditions and triggers at which the data is exchanged between the server and the data collection device.

In yet further embodiments, the exchange request is transmitted from the smart device to the data collection device via BLUETOOTH while the key pairs and the exchange configuration are transmitted from the server to the smart device via internet.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION OF THE SEVERAL VIEWS OF THE DRAWINGS

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete, and will fully convey the scope of this invention to those skilled in the art. In the description, details of well-known features and techniques may be omitted to avoid unnecessarily obscuring the presented embodiments.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of embodiments of the present invention, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements of various embodiments of the present invention.

Embodiments of the present invention disclosure a method, computer program product, and system for a secure device relay. As will be described in greater detail herein, the present invention provides a means to securely retrieve information from a data collection device via an application based on authorization by an external, server-driven access code that restricts the type of information and decryption keys used per application or device. Key benefits of the present invention include increased flexibility and granular control over the types of data made availability to certain applications or devices, the ability to personally manage device data, and a reduced chance of keys being compromised. In addition, the present invention allows for keys to be more easily revoked if compromised and a more secure control over the activation of devices. Detailed implementation of the present invention follows.

Figure 1:
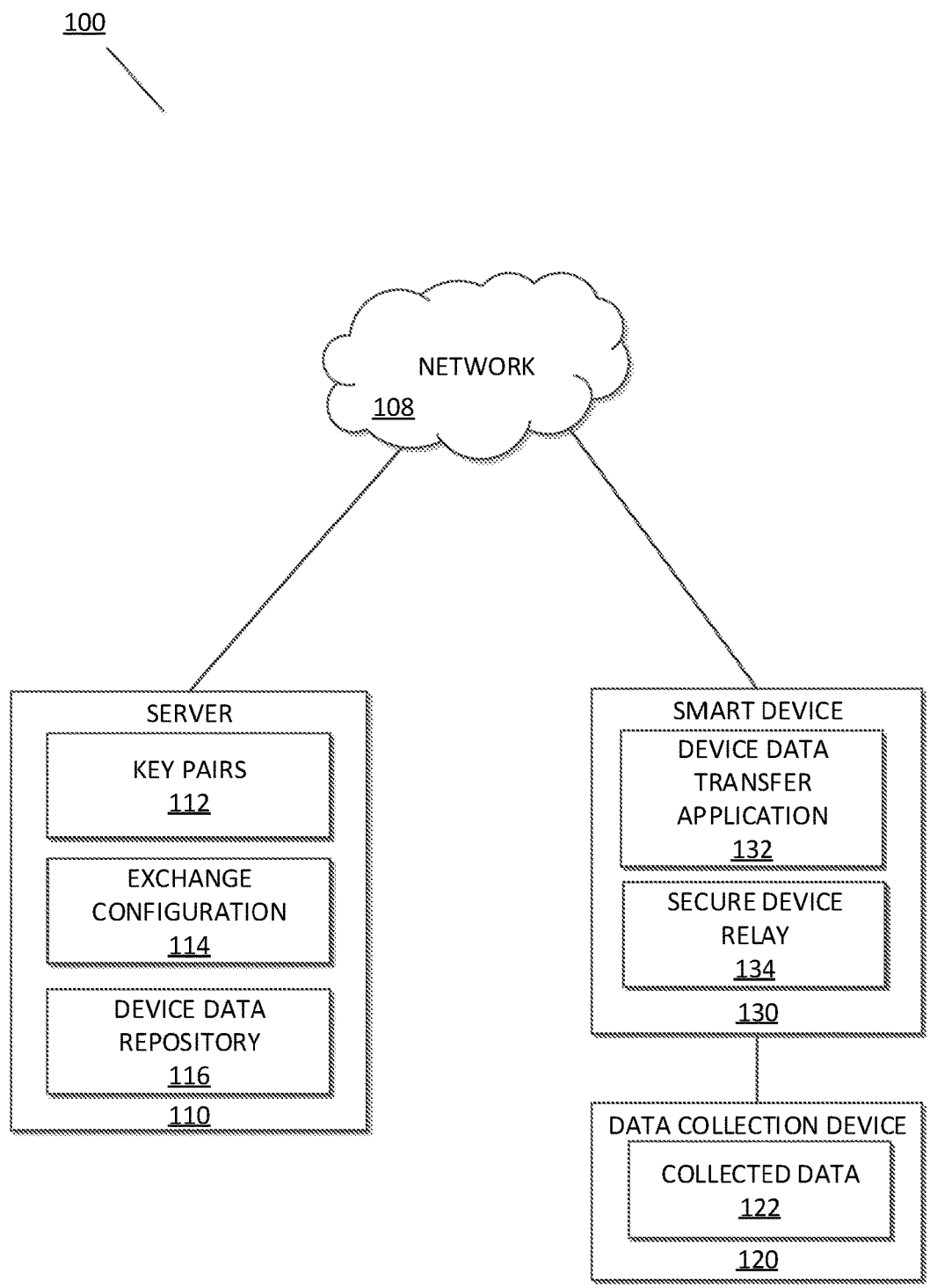
FIG. 1 depicts a schematic diagram of a secure device relay system 100, in accordance with an embodiment of the present invention.

FIG. 1 depicts a secure device relay system 100, in accordance with embodiments of the present invention. In the example embodiment, the secure device relay system 100 includes a server 110, a data collection device 120, and a smart device 130. While, in the example embodiment, programming and data of the present invention are stored and accessed remotely across several servers via the network 108, in other embodiments, programming and data of the present invention may be stored locally on as few as one physical computing device or amongst other computing devices than those depicted. For example, one skilled in the art may appreciate that while the secure device relay 134 is stored on smart device 130 in the example embodiment, the secure device relay 134 may be operable from the server 110, the data collection device 120, or hardware not depicted by the secure device relay system 100 of FIG. 1 in other embodiments.

In the example embodiment, the network 108 is a communication channel capable of transferring data between connected devices. In the example embodiment, the network 108 is the Internet, representing a worldwide collection of networks and gateways to support communications between devices connected to the Internet. Moreover, the network 108 may include, for example, wired, wireless, and/or fiber optic connections which may be implemented as an intranet network, a local area network (LAN), a wide area network (WAN), or a combination thereof. In further embodiments, the network 108 may be a BLUETOOTH network, a WiFi network, or a combination thereof. In yet further embodiments, the network 108 may be a telecommunications network used to facilitate telephone calls between two or more parties comprising a landline network, a wireless network, a closed network, a satellite network, or a combination thereof. In general, the network 108 can be any combination of connections and protocols that will support communications between connected devices.

In the example embodiment, the server 110 includes one or more key pairs 112, an exchange configuration 114, and a device data repository 116. The server 110 may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, or any other electronic device or computing system capable of receiving and sending data to and from other computing devices. While the server 110 is shown as a single device, in other embodiments, the server 110 may be comprised of a cluster or plurality of computing devices, working together or working separately. The server 110 is described in greater detail with reference to FIG. 4.

In the example embodiment, the key pairs 112 are digit sets used to secure communications through encryption in a practice known as cryptography. In the example embodiment, the secure device relay system 100 utilizes encryption to ensure that data communicated between devices is available only to approved parties. Specifically, in the example embodiment, the secure device relay system 100 implements asymmetric encryption wherein data encrypted with a public key is decryptable only by a user having a corresponding private key. In other embodiments, however, the secure device relay system 100 may implement other encryption techniques. While in the example embodiment the key pairs 112 are generated and stored on the server 110, in other embodiments the key pairs 112 may be generated and stored elsewhere in a certificate manager.

In the example embodiment, the exchange configuration 114 defines access control(s) for certain applications and devices with respect to certain data. The exchange configuration 114 utilizes access codes, or configuration items, in order to limit a type, amount, frequency, etc. at which the device data transfer application 132 may exchange the collected data 122 with the data collection device 120. For example, configuration items corresponding to data type may include diagnosis information (e.g., patient diagnosis, diagnosis stage, etc.), patient data (e.g., required medications, required measurements, measurement values, etc.), and device status (e.g., battery level, medicine level, etc.). Similarly, configuration items corresponding to data amount may include a number of individual measurements (e.g., one, two, etc.), a quantity of data (e.g., 1 MB, etc.), and the like. Moreover, configuration items for frequency may be defined at a prescribed interval (e.g., once per hour/day/week/etc.) or be based on conditions that need be satisfied and triggers that need be activated. For example, the configuration items for frequency may be defined as after each use of the data collection device 120, following measurement levels exceeding/dropping below a threshold, user/physician approval/consent, user input, detection of specified events, etc.

In the example embodiment, the device data repository 116 is a collection of information contained in files, folders, and other document types. In the example embodiment, the device data repository 116 may be a corpora of documents which detail bodies of categorized and subject specific data, such as medical, legal, and financial data. In other embodiments, the data device repository may include uncategorized data of miscellaneous topics. In the example embodiment, the device data repository 116 may be structured (i.e. have associated metadata), partially structured, or unstructured. Moreover, data within the device data repository 116 may be written in programming languages of common file formats such as .csv, .docx, .doc, .pdf, .rtf, etc. In other embodiments, the device data repository 116 may include handwritten and other documents scanned or otherwise converted into electronic form.

In the example embodiment, the data collection device 120 includes one or more collected data 122, and may be any device capable of collecting, storing, processing, and transmitting data. In embodiments, for example, the data collection device 120 may be a device within an environment, such as a smart device, appliance, sensor, camera, microphone, etc. In other embodiments, the data collection device 120 may be a wearable, such as glasses, a contact lens, watch/wristband, ring, anklet, headband, mouthpiece, and the like. In further embodiments, the data collection device 120 may be a special purpose-device such as an insulin pen, pacemaker, catheter, meter, implantable device, etc. Moreover, in embodiments, the data collection device 120 may include computing components used for collecting, processing, aggregating, and transmitting data, for example those depicted by FIG. 4. While the data collection device 120 is shown as a single device, in other embodiments, the data collection device 120 may be comprised of a cluster or plurality of computing devices, working together or working separately.

In the example embodiment, the collected data 122 is data collected by and stored on the data collection device 120. In the example embodiment, the collected data 122 may include data contained in files, folders, and other document types and may be structured (i.e., organized into a formatted repository), partially structured, or unstructured. The collected data 122 may be written in programming languages of common file formats such as csv, .docx, .doc, .pdf, .rtf, etc. In embodiments, such data may be owned by the user of the data collection device 120, and therefore transfer of the collected data 122 may be subject to consent and privacy laws. Accordingly, the collected data 122 may be held to strict security standards and encrypted, when necessary.

In the example embodiment, the smart device 130 includes a device data transfer application 132 and a secure device relay 134. In embodiments, the smart device 130 may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, or any other electronic device or computing system capable of receiving and sending data to and from other computing devices. While the smart device 130 is shown as a single device, in other embodiments, the smart device 130 may be comprised of a cluster or plurality of computing devices, working together or working separately. The smart device 130 is described in greater detail with reference to FIG. 4.

In the example embodiment, the device data transfer application 132 is a software and/or hardware application capable of transferring the collected data 122 from the data collection device 120 to the device data repository 116 on the server 110. In embodiments, the device data transfer application 132 utilizes various wired and wireless connection protocols for data transmission and exchange, including BLUETOOTH, 2.4 gHz and 5 gHz internet, near-field communication, Z-Wave, Zigbee, etc. For example, the device data transfer application 132 may utilize BLUETOOTH to transfer the collected data 122 from the data collection device 120 to the smart device 130, and an internet connection to transmit the collected data 122 from the smart device 130 to the server 110. In other embodiments, however, the secure device relay system 100 may implement alternative data transfer techniques and methodologies.

In the example embodiment, the secure device relay 134 is a software/hardware component capable of, among other things, receiving or intercepting a request by a smart device to exchange collected data from a data collection device and extracting information regarding the exchange request. In addition, the secure device relay 134 is capable of determining whether the exchange is registered and, if not, registering the requested exchange by submitting the registration information to and retrieving a key pair/exchange configuration from a server. The secure device relay 134 is further capable of determining whether the exchange request is permitted by the exchange configuration and, if so, processing the data exchange.

Figure 2:
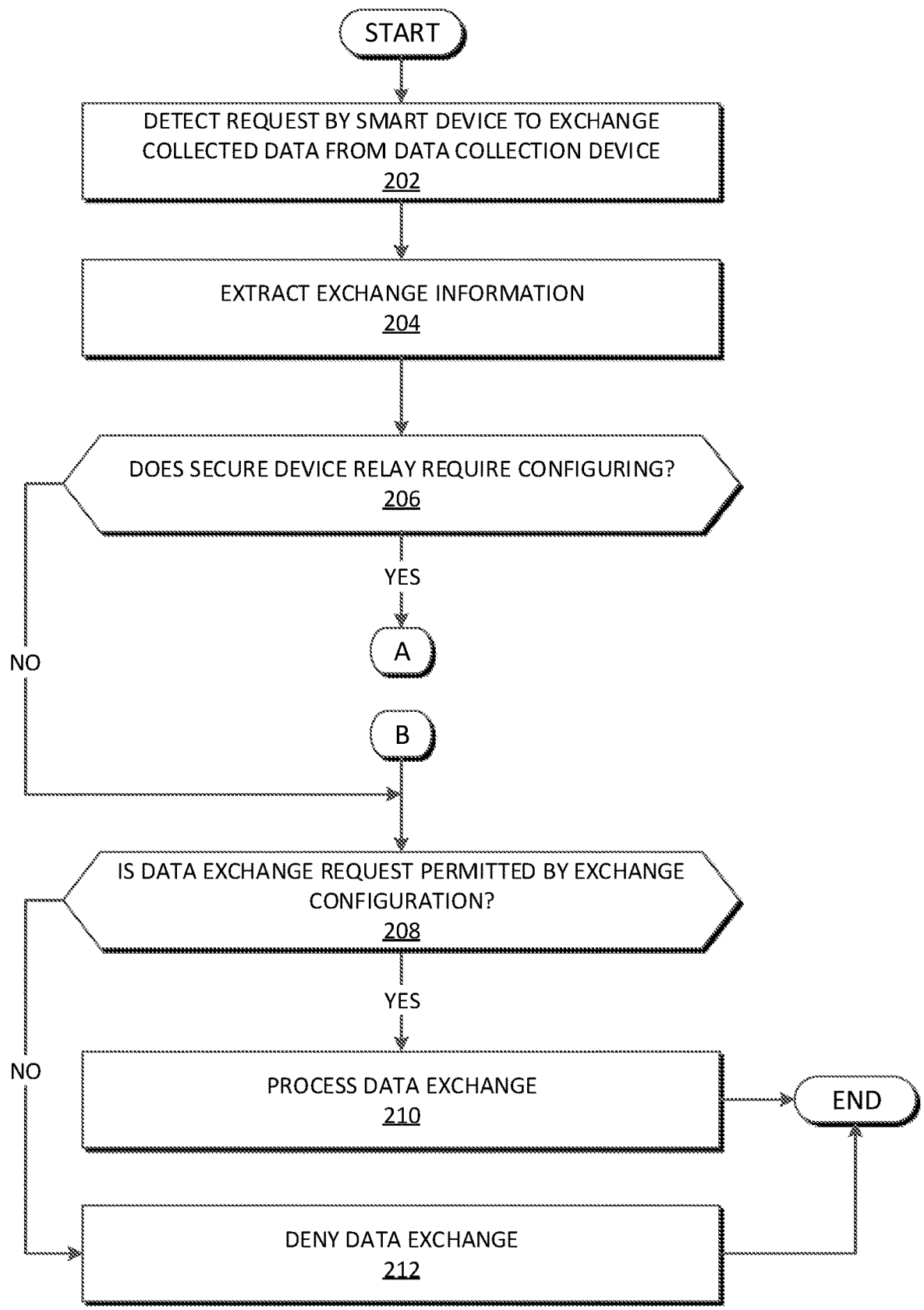
FIG. 2 depicts a flowchart illustrating the operations of a secure device relay application 134 of the secure device relay system 100 in securely exchanging user data between a data collection device and mobile device, in accordance with an embodiment of the present invention.

FIG. 2 illustrates the operations of the secure device relay 134 of the secure device relay system 100 in securely transferring data from a data collection device 120 to a server 110 using a smart device 130, in accordance with an embodiment of the present invention.

The secure device relay 134 intercepts or receives a request made by a smart device or an application on a smart device to exchange collected data with a data collection device (step 202). In the example embodiment where the device data transfer application 132 is configured to on-demand and/or periodically exchange the collected data 122 with the device data repository 116, the secure device relay 134 detects a request for exchange by monitoring connection channels between the smart device 130 and the data collection device 120. For example, the secure device relay 134 may monitor frequencies of communication channels such as BLUETOOTH, wired/wireless internet, near-field communication, Z-Wave, Zigbee, wired data transfer, and other communication channels capable of transferring data. In other embodiments, the secure device relay 134 may detect an exchange request via integration with the device data transfer application 132 such that initialization of any exchange request is detected and intercepted by the secure device relay 134. In yet further embodiments, the secure device relay 134 may detect an exchange request by receiving a request via user input.

To further illustrate the operations of the secure device relay 134, reference is now made to an illustrative example where an insulin pen (the data collection device 120) connects via BLUETOOTH to a smart phone (the smart device 130) in order to transfer insulin injection and glucose level data (the collected data 122) to a doctor (the device data repository) via a smart phone app (the device data transfer application 132). In this example, the secure device relay 134 is configured to monitor the smart phone application facilitating the transfer and intercept any data request(s) to exchange data with the insulin pen via BLUETOOTH.

The secure device relay 134 extracts exchange information (step 204). In the example embodiment, the secure device relay 134 extracts information necessary to identify, or register if not already registered, the requested exchange. Such information may include an identity of the data collection device 120, an application type of the device data transfer application 132, and an amount/type/frequency of collected data 122 requested by the device data transfer application 132. The secure device relay 134 then utilizes the extracted information in order to perform actions with respect to the device data transfer application 132, such as register the exchange configuration with the server 110 (described in greater detail with respect to FIG. 3), validate an exchange request, limit a data exchange, add/revoke exchange credentials, etc. Such information may include an identifier associated with the data collection device 120 (e.g., a MAC address), an identifier associated with the device data transfer application 132 (e.g., an application name/serial number), and an amount/type/frequency at which the collected data 122 is exchanged with the device data transfer application 132. In other embodiments, the exchange configuration 114 may further include information regarding what types of the collected data 122 is collected by the data collection device 120, conditions/triggers for exchange, where geographically and with whom the data may be exchanged, protocols to exchange information in accordance with relevant private/public data regulations, and the like.

With reference again to the previously introduced example, after detecting a data exchange request, the secure device relay 134 extracts information needed to identify/register the requested exchange. Such extracted information includes a MAC address associated with the insulin pen, data types that include an insulin shot and glucose level, a serial number associated with the smart phone app, and the request that one insulin shot measurement and one glucose measurement are provided after each insulin pen use. In some embodiments with more demanding requests, the request may further request diagnosis information, how many shots are left in the insulin pen, a level of medicine, an amount of charge left on the device, etc.

The secure device relay 134 determines whether a secure device relay requires configuring (decision 206). In the example embodiment, the secure device relay 134 determines whether the requested exchange need be initially configured with the exchange configuration 114, or whether the secure device relay need be reconfigured due to, e.g., expired token(s), time lapse, contract lapse, added/revoked credentials, compromised keys/breach, etc. Here, the secure device relay 134 determines whether the secure device relay requires reconfiguring by verifying that the device data transfer application 132, as well as the data being requested, are registered within the exchange configuration 114. Moreover, after having been initially registered/configured, the secure device relay 134 will then periodically verify the registration and check the server 110 for updated exchange configuration information and/or key pair encryption information.

Referring now to the previously introduced, illustrative example, the secure device relay 134 determines whether the insulin pen MAC address, the data types of insulin shot and glucose level, the serial number of the app, and requested data of one insulin shot measurement and one glucose level measurement after each use are registered with the server 110.

Figure 3:
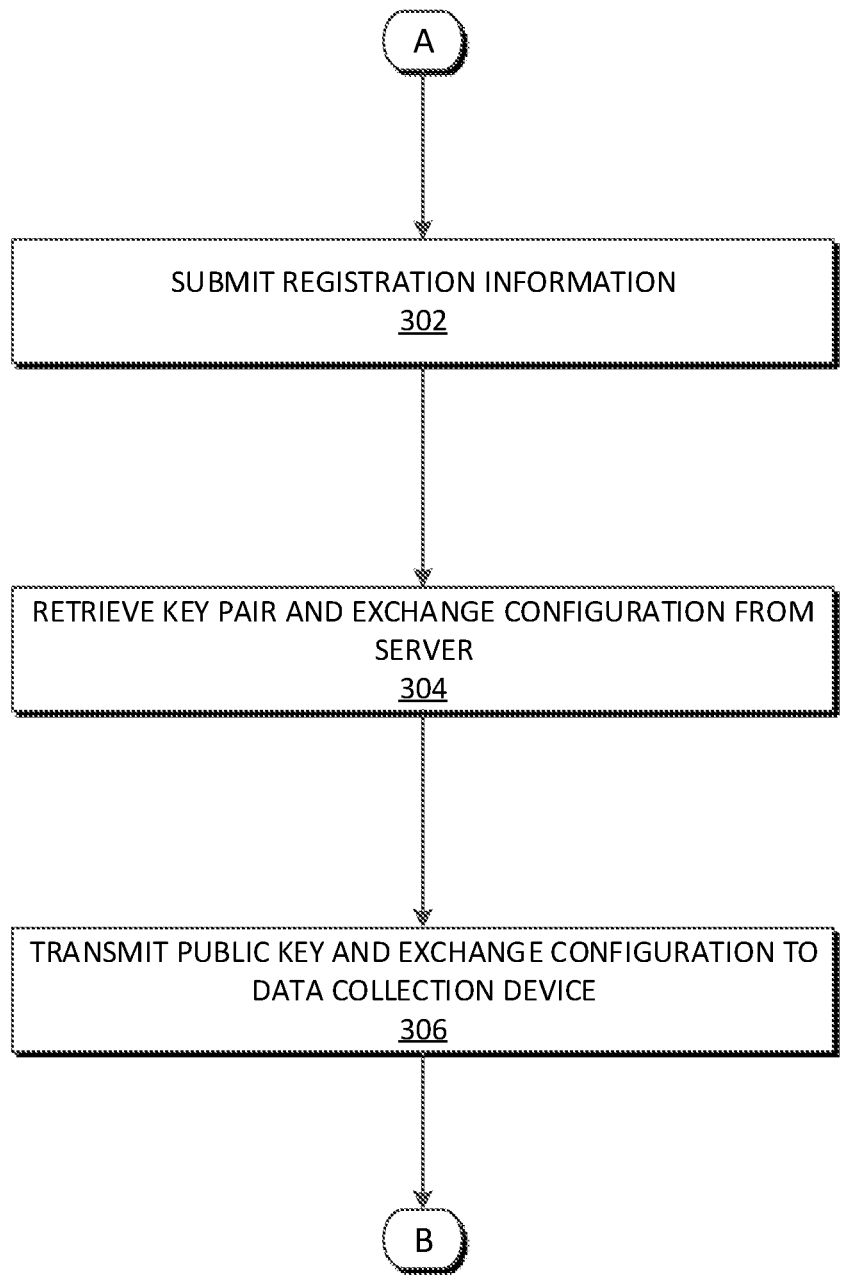
FIG. 3 depicts a flowchart illustrating the operations of the secure device relay 134 of the secure device relay system 100 in configuring a data exchange, in accordance with an embodiment of the present invention.

If the secure device relay 134 determines that the secure device relay requires configuring (decision 206, "YES" branch), then the secure device relay 134 proceeds to the process of configuring the secure device relay as illustrated by steps 302-306 of FIG. 3 and, in particular, submitting the extracted exchange registration information to the server (step 302). In the example embodiment, registering the requested data exchange, including devices, measurements, etc., ensures that data transfer between the data collection device 120 and the server 110 are in accordance with permissions provided to the device data transfer application 132. Accordingly, recording information such as the data collection device 120 MAC address, the device data transfer application 132 serial number, and the smart device 130 MAC address allows the secure device relay 134 to monitor and modify the permissions provided to the device data transfer application 132 in real time. Moreover, the secure device relay 134 verifies the authenticity of the registration request by providing with this information a digital signature corresponding to the smart device 130 to the server 110. This form of authentication between the secure device relay 134 and data collection device 120 provides mutual authentication with SSL certificates when communicating with the server 110 and both will mutually authenticate and authorize each other to access the registration services and exchange information services. During the registration process, the secure device relay 134 may further seek registration approval/consent from necessary parties, such as a user of the data collection device 120 or physician, as needed. Such approval may be sought via phone, email, push notification, etc., and be required upon initial configuration and/or as permissions within the exchange configuration 114 are modified.

With reference again to the illustrative example, the secure device relay 134 transmits the MAC addresses corresponding to the data collection device 120 and the smart device 130 to the server 110, along with a digital signature of the smart device 130 verifying the authenticity of the registration. In embodiments, the registration information may further include details regarding the requested exchange, such as the types, amount, and exchange frequency of the data.

The secure device relay 134 retrieves a key pair and exchange configuration from the server (step 304). In the example embodiment, a key pair of the key pairs 112 is retrieved from the server 110 and the keys implement asymmetric encryption wherein data is encrypted using a public key and decrypted using a private key. Using encryption methods such as the above allow for a secure transfer of data, and thereby prevent unauthorized or adversarial parties from gaining access to the data. In addition, the secure device relay 134 retrieves an exchange configuration from the server 110 defining access permissions of the data transfer application 132 with respect to the collected data 122. As mentioned above, and with respect to the device data transfer application 132 exchanging the collected data 122 with the device data repository 116, the exchange configuration may define an amount/type of data, a time/place/frequency for exchange, triggers/conditions/requirements for exchange, approval/consent by specific parties, etc. In the example embodiment, the secure device relay 134 retrieves the key pair and exchange configuration using an internet connection, however in other embodiments may utilize other forms of data transfer.

Returning to the previously introduced example, the secure device relay 134 retrieves an asymmetric key pair from the server and an exchange configuration indicating that the device data transfer application 132 may exchange insulin shot and glucose level data after each use of the insulin pen.

The secure device relay 134 transmits a public key of the key pair and the exchange configuration to the data collection device (step 306). In the example embodiment, the data collection device 120 utilizes the public key to encrypt data exchange communications between the data collection device 120 and the smart device 130. Moreover, the data collection device 120 utilizes the exchange configuration in order to limit the exchange of the collected data 122 by the device data transfer application. While in the example embodiment this transfer is performed via BLUETOOTH, in other embodiments the transfer may be performed via other data transfer means. In the example embodiment, step 306 concludes the exchange registration process illustrated by FIG. 3. As needed, however, the secure device relay 134 may return to the configuration process of FIG. 3 for the purposes of registering additional exchanges, modifying/revoking existing exchanges, retrieving updated key pairs and exchange configurations, etc.

Furthering the example introduced above, the secure device relay 134 transmits a public key of the retrieved key pair and the retrieved exchange configuration to the insulin pen.

Returning again to FIG. 2, after configuring/reconfiguring the secure device relay (steps 302-306) or determining that the secure device relay does not require configuration (decision 206, "NO" branch), the secure device relay 134 determines whether the data exchange request is permitted by the exchange configuration (decision 208). In the example embodiment, the requested data exchange is compared to the registered exchange configuration(s) to determine whether the requested exchange is permitted. As the exchange configuration has been transmitted between components, the exchange configuration is now accessible to the server 110, the data collection device 120, and the smart device 130. Accordingly, any device of the example embodiment is capable of applying the access controls prescribed by the exchange configuration. In the example embodiment, however, it is preferable that the data is limited at the source in order to limit potential for exposure. Accordingly, the secure device relay 134 instructs the data collection device 120 to only allow for data exchanges permitted by the exchange configuration. In other embodiments, however, this determination may be made at the smart device 130 or the server 110 depending on objectives and constraints of the system, such as privacy concerns and processing power of the data collection device 120.

Referring to the example mentioned above, the data collection device 120 compares the data exchange request of insulin and glucose level data after each insulin pen use to the retrieved exchange configuration.

If the secure device relay 134 determines that the data exchange request is within the exchange configuration (decision 208, "YES" branch), then the secure device relay 134 processes the data exchange (step 210).

Furthering the example above, the secure device relay 134 permits the transfer of the insulin and glucose level data following each insulin pen use.

If the secure device relay 134 determines that the data exchange request is not within the exchange configuration (decision 208, "NO" branch), then the secure device relay 134 may be configured to take additional action. Such action may include simply recording denial of the exchange, notifying a user of the data collection device 120, notifying a physician of the user, requesting consent from an individual such as the user/physician, etc. In embodiments where permission to exchange partial information is permitted by the exchange configuration 114, the secure device relay 134 may be configured to only exchange such approved data.

Figure 4:
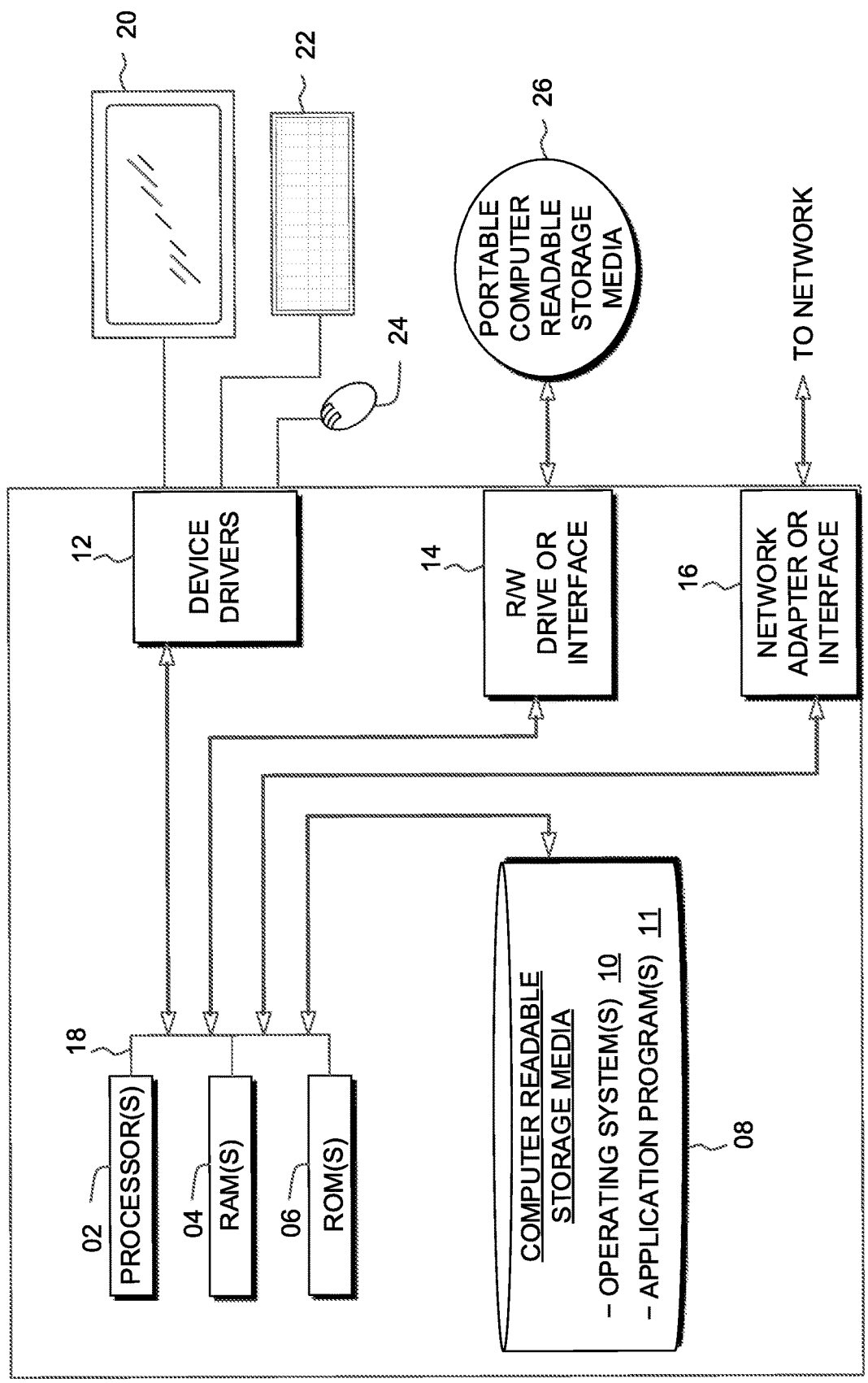
FIG. 4 illustrates a block diagram depicting the hardware components of the secure device relay system 100 of FIG. 1, in accordance with an example embodiment of the present invention.

FIG. 4 depicts a block diagram of devices within the secure device relay system 100 of FIG. 1, in accordance with an embodiment of the present invention. It should be appreciated that FIG. 4 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Based on the foregoing, a computer system, method, and computer program product have been disclosed. However, numerous modifications and substitutions can be made without deviating from the scope of the present invention. Therefore, the present invention has been disclosed by way of example and not limitation.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
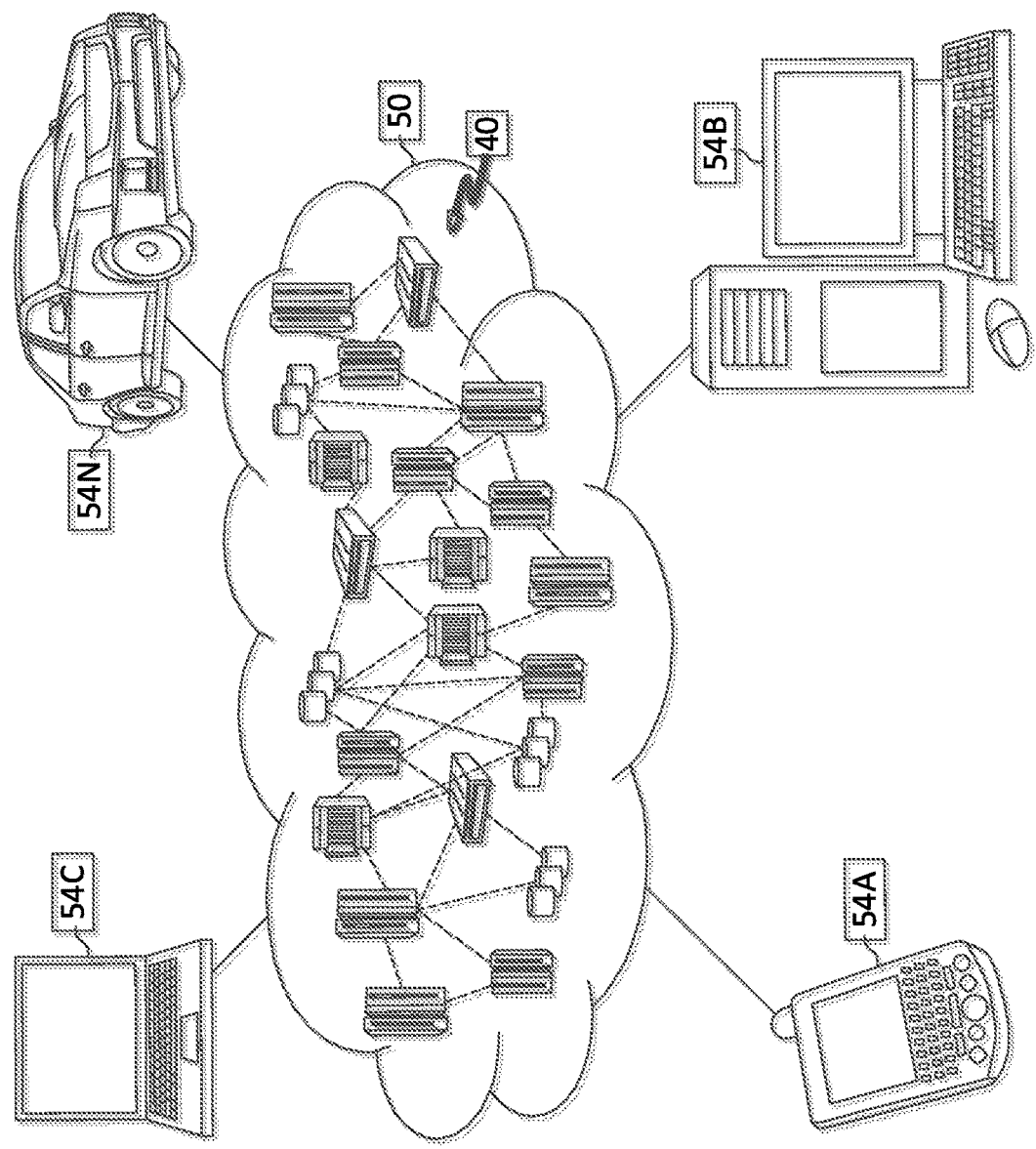
FIG. 5 depicts a cloud computing environment, in accordance with an embodiment of the present invention.

Referring now to FIG. 5, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 40 and cloud computing environment 50 can communicate with any type of computerized device over any type of network and/or network addressable connection (e.g., using a web browser).

Figure 6:
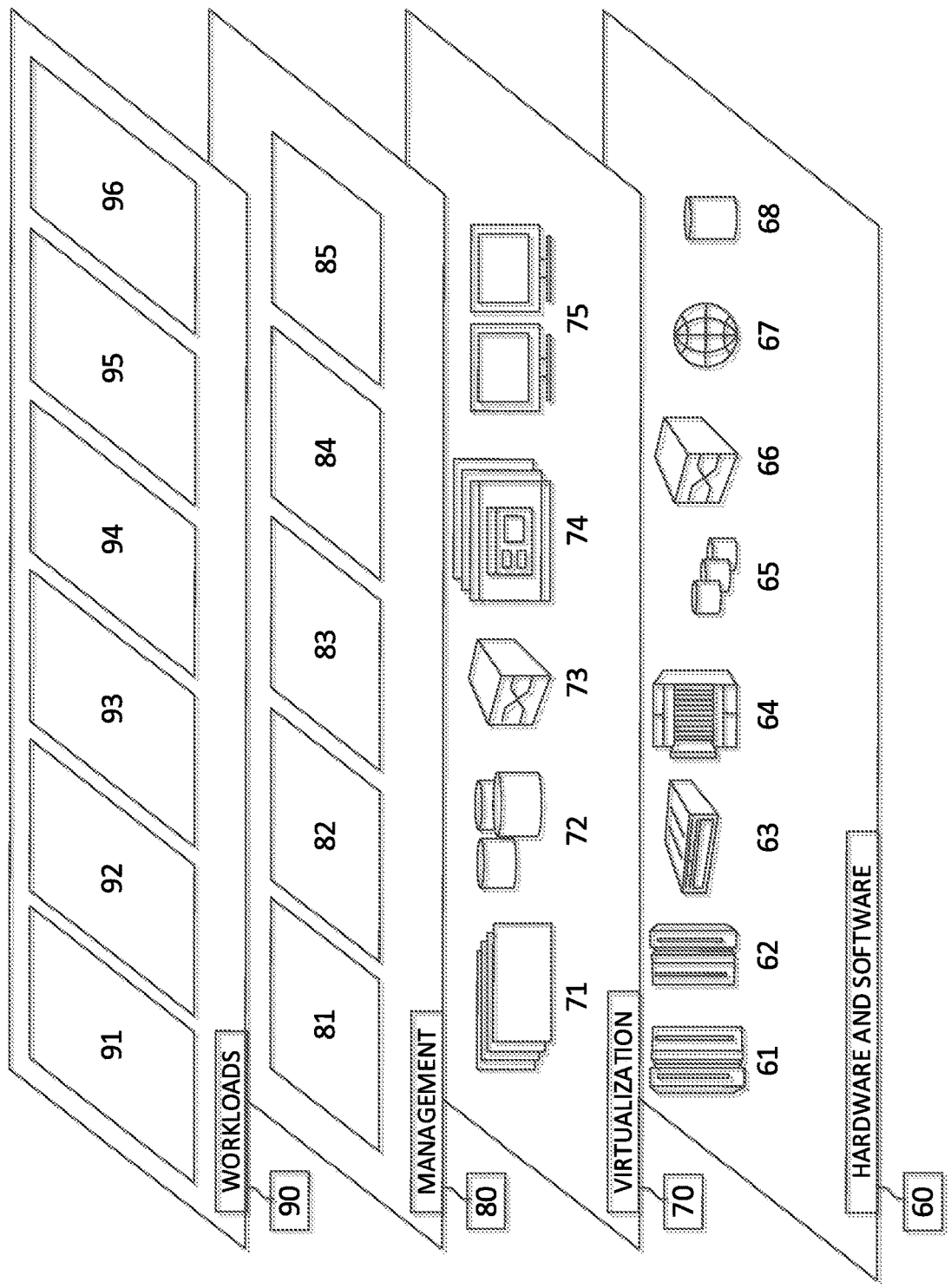
FIG. 6 depicts abstraction model layers, in accordance with an embodiment of the present invention.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for providing a secure device relay between a data collection device and a server using a smart device, the method comprising: transmitting to a server a unique identifier corresponding to a data collection device and a digital signature corresponding to a smart device;
   receiving from the server an asymmetric key pair and an exchange configuration defining access control to data stored on the data collection device, wherein the exchange configuration includes data exchange regulations associated with a geographic area in which the data may be exchanged;
   transmitting to the data collection device a public key of the received asymmetric key pair and the exchange configuration;
   detecting an exchange request to exchange the data between the server and the data collection device;
   determining whether the exchange request is permitted based on the exchange configuration; and
   based on determining that the exchange request is permitted by the exchange configuration, processing the request.

2. The computer-implemented method of claim 1, further comprising:
   based on determining that the exchange request is not permitted by the exchange configuration, denying the exchange request and performing an action selected from a group comprising:
   notifying a user of the data collection device, notifying a physician of the user, and requesting consent to process the exchange from the user.

3. The computer-implemented method of claim 1, further comprising:
   receiving a request to modify access controls defined by the exchange configuration;
   obtaining consent to the requested modification from a user of the data collection device; and
   modifying the exchange configuration.

4. The computer-implemented method of claim 1, wherein the exchange configuration further defines access control with respect to a type of the data, an amount of the data, and a frequency at which the data is exchanged between the server and the data collection device.

5. The computer-implemented method of claim 4, wherein the exchange configuration further defines access control with respect to conditions and triggers at which the data is exchanged between the server and the data collection device.

6. The computer-implemented method of claim 1, wherein the exchange request is transmitted from the smart device to the data collection device via short range communication while the key pairs and the exchange configuration are transmitted from the server to the smart device via internet.

7. A computer program product for providing a secure device relay between a data collection device and a server using a smart device, the computer program product comprising:
   one or more non-transitory computer-readable storage media and program instructions stored on the one or more non-transitory computer-readable storage media capable of performing a method, the method comprising:
   transmitting to a server a unique identifier corresponding to a data collection device and a digital signature corresponding to a smart device;
   receiving from the server an asymmetric key pair and an exchange configuration defining access control to data stored on the data collection device, wherein the exchange configuration includes data exchange regulations associated with a geographic area in which the data may be exchanged;
   transmitting to the data collection device a public key of the received asymmetric key pair and the exchange configuration;
   detecting an exchange request to exchange the data between the server and the data collection device;
   determining whether the exchange request is permitted based on the exchange configuration; and
   based on determining that the exchange request is permitted by the exchange configuration, processing the request.

8. The computer program product of claim 7, further comprising:
   based on determining that the exchange request is not permitted by the exchange configuration, denying the exchange request and performing an action selected from a group comprising:
   notifying a user of the data collection device, notifying a physician of the user, and requesting consent to process the exchange from the user.

9. The computer program product of claim 7, further comprising:
   receiving a request to modify access controls defined by the exchange configuration;
   obtaining consent to the requested modification from a user of the data collection device; and
   modifying the exchange configuration.

10. The computer program product of claim 7, wherein the exchange configuration further defines access control with respect to a type of the data, an amount of the data, and a frequency at which the data is exchanged between the server and the data collection device.

11. The computer program product of claim 10, wherein the exchange configuration further defines access control with respect to conditions and triggers at which the data is exchanged between the server and the data collection device.

12. The computer program product of claim 7, wherein the exchange request is transmitted from the smart device to the data collection device via short range communication while the key pairs and the exchange configuration are transmitted from the server to the smart device via internet.

13. A computer system for providing a secure device relay between a data collection device and a server using a smart device, the computer system comprising:
   one or more computer processors, one or more computer-readable storage media, and program instructions stored on one or more of the computer-readable storage media for execution by at least one of the one or more processors capable of performing a method, the method comprising:

transmitting to a server a unique identifier corresponding to a data collection device and a digital signature corresponding to a smart device;

receiving from the server an asymmetric key pair and an exchange configuration defining access control to data stored on the data collection device, wherein the exchange configuration includes data exchange regulations associated with a geographic area in which the data may be exchanged;

transmitting to the data collection device a public key of the received asymmetric key pair and the exchange configuration;

detecting an exchange request to exchange the data between the server and the data collection device;

determining whether the exchange request is permitted based on the exchange configuration; and based on determining that the exchange request is permitted by the exchange configuration, processing the request.

14. The computer system of claim 13, further comprising:
based on determining that the exchange request is not permitted by the exchange configuration, denying the exchange request and performing an action selected from a group comprising:
notifying a user of the data collection device, notifying a physician of the user, and requesting consent to process the exchange from the user.

15. The computer system of claim 13, further comprising:
receiving a request to modify access controls defined by the exchange configuration;
obtaining consent to the requested modification from a user of the data collection device; and
modifying the exchange configuration.

16. The computer system of claim 13, wherein the exchange configuration further defines access control with respect to a type of the data, an amount of the data, and a frequency at which the data is exchanged between the server and the data collection device.

17. The computer system of claim 16, wherein the exchange configuration further defines access control with respect to conditions and triggers at which the data is exchanged between the server and the data collection device.

* * * * *